United States Patent [19]

Yamamoto et al.

[11] 4,185,034
[45] Jan. 22, 1980

[54] BLEACHING OLEFIN SULFONATES WITH PHOSPHATE AND PEROXIDE

[75] Inventors: Kazuo Yamamoto, Kodaira; Shizuo Sekiguchi, Yokohama; Yozo Miyawaki, Chiba, all of Japan

[73] Assignee: Lion Fat & Oil Co., Ltd., Tokyo, Japan

[21] Appl. No.: 903,396

[22] Filed: May 8, 1978

Related U.S. Application Data

[63] Continuation of Ser. No. 686,382, May 14, 1976, abandoned.

[30] Foreign Application Priority Data

May 23, 1975 [JP]  Japan .................................. 50-62390

[51] Int. Cl.$^2$ ........................................... C07C 143/02
[52] U.S. Cl. .................................................. 260/513 R
[58] Field of Search ................................. 260/513 R

[56] References Cited

U.S. PATENT DOCUMENTS

| 2,738,365 | 3/1956 | Sylvester | 260/505 P |
| 2,804,466 | 8/1957 | Schurman | 260/513 R |
| 3,997,575 | 12/1976 | Ogoshi et al. | 260/513 R |

FOREIGN PATENT DOCUMENTS 983056  2/1965  United Kingdom .

Primary Examiner—Joseph E. Evans
Attorney, Agent, or Firm—Blanchard, Flynn, Thiel, Boutell & Tanis

[57] ABSTRACT

A method of bleaching olefin sulfonates, which comprises adding more than 0.1% by weight of hydrogen peroxide, with more than 0.1% by weight of phosphate alone or silicate alone or a mixture of the two, to an olefin sulfonate having 12 to 22 carbon atoms, and treating at a temperature in the range of from 30° to 130° C.

5 Claims, No Drawings

BLEACHING OLEFIN SULFONATES WITH PHOSPHATE AND PEROXIDE

This is a continuation, of application Ser. No. 636,382 filed May 14, 1976 and now abandoned.

BACKGROUND OF THE INVENTION

As the method of bleaching olefin sulfonates, a bleaching method employing hypochlorite is most popular, and the bleaching effect thereof is admittedly great. However, a bleaching method employing hypochlorite is attended with various troubles with respect to the bleaching treatment including sodium chloride is produced as a by-product at the time of bleaching, corrosion of the apparatus used for bleaching takes place, etc.

There is also known a bleaching method employing hydrogen peroxide as disclosed in British Pat. No. 983,056 as the bleaching agent for olefin sulfonates. But, this method is inferior in bleaching effect compared with the foregoing method employing hypochlorite, and a satisfactory bleaching effect cannot be attained when it is put to practical use.

SUMMARY OF THE INVENTION

The present invention provides an improved method of bleaching olefin sulfonates by hydrogen peroxide. The breaching mechanism of the hydrogen peroxide is not clarified, but it is said that $HO_2^-$ ion arising from the decomposition of hydrogen peroxide, oxygen in the nascent state, etc. take part in the reaction. For instance, Gustaf Holst have disclosed the fact that hydrogen peroxide displays an oxidation effect through the reactions expressed by the formulae (1) and (2) below in an aqueous solution of alkali, and in the bleaching reaction, said hydrogen peroxide removes electrons of colored impurities as expressed by the formula (2) thereby to effect bleaching.

$$H_2O_2 \rightleftharpoons H^+ + HO_2^- \tag{1}$$

$$HO_2^- + H_2O + 2e \rightleftharpoons 3OH^- \tag{2}$$

Meanwhile, in an aqueous solution of an alkali, there simultaneously takes place a reaction expressed by the following formula $$HO_2^- + OH^- \rightleftharpoons H_2O + O_2 + 2e \tag{3}$$

and a part of the electrons to be consumed in the formula (2) is supplied while oxygen gas is given forth, resulting in a lowering of the bleaching efficiency.

Therefore, in order to make the bleaching work progress efficiently, it suffices to control the decomposition of hydrogen peroxide so as to make the reaction in the formula (2) take part in the bleaching reaction preferentially. The present invention renders it possible to perform the control of such reaction by the addition of a specific catalytic substance, and this specific substance is supposed to function very effectively in bleaching work for olefin sulfonates while controlling the generation of oxygen gas in the presence of hydrogen peroxide. The specific substance herein means an individual phosphate or silicate or a mixture of the two, and the present invention is intended to improve the effect of bleaching olefin sulfonates by adding said specific substance together with hydrogen peroxide to an olefin sulfonate while maintaining a prescribed reaction temperature.

The olefin sulfonates in the present invention are olefin sulfonates obtained by subjecting α-olefins having 12 to 22 carbon atoms or vinylidene type olefins to sulfonation by a known method, followed by neutralization with caustic alkali and hydrolysis. As to the method of sulfonation, any of the well-known methods will do.

The phosphate applicable to the present invention includes sodium tripolyphosphate, potassium tripolyphosphate, sodium pyrophosphate, potassium pyrophosphate, sodium phosphate and potassium phosphate. And, the silicate applicable to the present invention includes various sodium silicates and potassium silicates. These phosphates and silicates can be employed either individually or both.

At the time of bleaching the olefin sulfonates, it is necessary to add hydrogen peroxide by more than 0.1% in an amount of weight relative to the α-olefin sulfonate, and a phosphate or a silicate or a mixture of the two in an amount of more than 0.1% by weight relative to the α-olefin sulfonate; a preferable amount of the hydrogen peroxide to be added is in the range of from 0.5 to 5% by weight and the preferable amount of the phosphate and/or silicate is in the range of from 2 to 7% by weight. In the case where the amount of hydrogen peroxide applied is less than 0.1% by weight, the bleaching effect is unsatisfactory, yet the hydrogen peroxide in an amount of more than 10% by weight would bring on no difference of the bleaching effect and is therefore not economical.

Also, on the occasion of performing the bleaching by adding hydrogen peroxide together with the phosphate and/or silicate to an olefin sulfonate, if the temperature for bleaching is below 30° C., much time will be required for the bleaching, and therefore it is inappropriate. While, in the case where the temperature for bleaching is above 130° C., there occurs a sudden decomposition of hydrogen peroxide rendering it difficult to make the bleaching work progress efficiently. Accordingly, the temperature for bleaching should be maintained in the range of from 30° to 130° C., preferably from 50° to 100° C. Besides, when the pH value of the aqueous solution of olefin sulfonate is adjusted to more than 5, preferably in the range of from 7 to 12, at the time of bleaching, the bleaching can be performed effectively. Further, as the presence of phosphate in the undissolved state within the treating liquid at the time of bleaching is undesirable, it is advisable to apply it as an aqueous solution, or, in the event of applying it in the state of powder, it is desirable to dissolve it thoroughly upon mixing with the treating liquid before the bleaching.

According to the bleaching method of the present invention as set forth above, the bleaching effect on olefin sulfonates is greater than that of the conventional bleaching employing hydrogen peroxide alone. Also, when compared with the bleaching method employing hypochlorite, the present method not only has an excellent bleaching effect equivalent to the method employing hypochlorite but also is free from such troubles as generation of sodium chloride as a by-product, occurrence of the corrosion of apparatus, etc. attendant upon the bleaching by means of hypochlorite. Particularly when said phosphate is applied, occurrence of the foaming phenomenon during bleaching work can be controlled, and when said silicate is applied, tne corrosion resistance of the apparatus can be enhanced. Therefore, in the case where both phosphate and silicate are applied jointly, a foam-controlling effect and corrosion resistance can be concurrently enhanced.

The effect of the present invention is further elucidated in the following by reference to concrete examples embodying the present invention. It will be understood, however, that the invention is not limited to the form of embodiments herein described by way of example, and can be modified in various ways without thereby exceeding the scope of the invention.

Example of synthesis:

α-olefin mixture 16 to 18 carbon atoms (mean molecular weight: about 235) are reacted with $SO_3$ in a molar ratio 1:1.14 in a thin film reactor, which is similar to the falling film type sulfonator disclosed Japanese Patent Publication No. 252/1967, at 40°–60° C. The rate of reaction was 95.3%.

Next, by adding 170 parts by weight of a 10% aqueous solution of caustic soda to 100 parts by weight of the resulting sulfonate, followed by neutralization and hydrolysis, a sodium salt of α-olefin sulfonate having 16 to 18 carbon atoms was prepared.

EXAMPLE 1

100 g of an aqueous solution of sodium salt of α-olefin sulfonate having 16 to 18 carbon atoms [active ingredient (hereinafter referred to as AI) concentration: 42% by weight, color tone (of 5% aqueous solution of AI: 600, pH value: 11] were first adjusted to have a pH value of 8 with 20% aqueous solution of sulfuric acid. Then, the solution was placed in a 300 ml-conical flask and heated up to a temperature of 80° C. Upon thus heating, sodium tripolyphosphate (to wit, a reagent powder) was added in an amount of 0.21 g (0.5% by weight relative to AI), followed by the addition of a 35% aqueous solution of $H_2O_2$ in an amount of 6 g (5 % by weight relative to AI) while stirring, and bleaching was performed by continuously stirring the mixture for 2 hours while maintaining the temperature thereof at 80° C. After finishing the bleaching, the pH value of the bleaching liquid was adjusted to 8 with 10% aqueous solution of NaOH, and the color tone of the thus obtained 5% aqueous solution of AI was measured. As a result, said color tone was 150. The conditions for measurement of the color tone were as set forth in the remarks for Table-1 to be shown later on.

EXAMPLES 2–17

By modifying the kind of phosphate or silicate and the amount thereof to be applied, the amount of aqueous solution of hydrogen peroxide to be added, the adjusted pH value of aqueous solution of sodium salt of α-olefin sulfonate having 16 to 18 carbon atoms and the time of bleaching in various ways as shown in Table-1, and applying the same procedures as in Example 1, the color tone of 5% aqueous solution of AI was measured. The result of said measurement was as shown in Table-1.

In this connection, in the case where sodium silicate was applied, the pH value was adjusted to 10 with 20% aqueous solution of sulfuric acid after adding sodium silicate.

COMPARATIVE EXAMPLE 1

100 g of the same sodium salt of α-olefin sulfonate having 16 to 18 carbon atoms as in the above examples were first adjusted to have a pH value of 8, and then placed in a 300 ml-conical flask and heated up to a temperature of 80° C. Subsequently, by adding a 35% aqueous solution of $H_2O_2$ in an amount of 6 g (5% by weight relative to AI), 2 hours' bleaching treatment was conducted while maintaining the temperature at 80° C. After finishing the bleaching, by adjusting the pH value of the bleaching liquid to 8 with a 10% aqueous solution of NaOH, the color tone of the thus obtained 5% aqueous solution of AI was measured. As a result, said color tone was 300.

COMPARATIVE EXAMPLE 2

Bleaching treatment was performed in the same way as in Comparative Example 1 except for the addition of sodium citrate in an amount of 2.1 g (or 5% by weight relative to AI) together with 6 g of a 35% aqueous solution of $H_2O_2$.

COMPARATIVE EXAMPLE 3

Bleaching was performed in the same way as in Comparative Example 1 except for the modification of the temperature for bleaching treatment to 50° C. and the time of bleaching to 3 hours.

COMPARATIVE EXAMPLE 4

Bleaching was performed in the same way as in Comparative Example 1 except for the modification of the temperature for bleaching treatment to 100° C.

COMPARATIVE EXAMPLE 5

Bleaching was performed in the same way as in Comparative Example 1 except for the addition of a 35% aqueous solution of $H_2O_2$ in an amount of 1.2 g (or 1% by weight relative to AI).

Table-1

|  | Comparative Example 1 | Comparative Example 2 | Example 1 | Example 2 | Example 3 |
| --- | --- | --- | --- | --- | --- |
| Additive (Applied amount: wt.% relative to AI) | — | sodium citrate (5) | sodium tripoly-phosphate (0.5) | sodium tripoly-phosphate (5) | sodium tripoly-phosphate (1) |
| Applied amount of $H_2O_2$ (wt.% relative to AI) | 5 | 5 | 5 | 5 | 5 |
| pH value of bleaching liquid | 8 | 8 | 8 | 8 | 8 |
| Temperature for bleaching treatment (°C.) | 80 | 80 | 80 | 80 | 80 |
| Time of bleaching (hr) | 2 | 2 | 2 | 2 | 2 |
| Color tone before bleaching (5% aqueous solution of AI) | 600 | 600 | 600 | 600 | 600 |

Table-1-continued

|  | Example 4 | Example 5 | Example 6 | Example 7 | Example 8 |
|---|---|---|---|---|---|
| Color tone after bleaching (5% aqueous solution of AI) | 300 | 280 | 150 | 90 | 130 |
| Additive (applied amount: wt.% relative to AI) | sodium tripoly-phosphate (3) | sodium tripoly-phosphate (7) | sodium tripoly-phosphate (10) | sodium tripoly-phosphate (7) | sodium secondary phosphate (5) |
| Applied amount of $H_2O_2$ (wt.% relative to AI) | 5 | 5 | 5 | 5 | 5 |
| pH value of bleaching liquid | 8 | 8 | 8 | 12 | 8 |
| Temperature for bleaching treatment (°C.) | 80 | 80 | 80 | 80 | 80 |
| Time of bleaching (hr) | 2 | 2 | 2 | 2 | 2 |
| Color tone before bleaching (5% aqueous solution of AI) | 600 | 600 | 600 | 600 | 600 |
| Color tone after bleaching (5% aqueous solution of AI) | 100 | 80 | 80 | 75 | 120 |

|  | Comparative Example 3 | Example 9 | Comparative Example 4 | Example 10 | Example 11 |
|---|---|---|---|---|---|
| Additive (applied amount: wt.% relative to AI) | — | sodium tripoly-phosphate (5) | — | sodium tripoly-phosphate (5) | sodium silicate (1) |
| Applied amount of $H_2O_2$ (wt.% relative to AI) | 5 | 5 | 5 | 5 | 5 |
| pH value of bleaching liquid | 8 | 8 | 8 | 8 | 10 |
| Temperature for bleaching treatment (°C.) | 50 | 50 | 100 | 100 | 80 |
| Time of bleaching (hr) | 3 | 3 | 2 | 2 | 2 |
| Color tone before bleaching (5% aqueous solution of AI) | 600 | 600 | 600 | 600 | 600 |
| Color tone after bleaching (5% aqueous solution of AI) | 380 | 150 | 280 | 75 | 110 |

|  | Example 12 | Example 13 | Comparative Example 5 | Example 14 | Example 15 |
|---|---|---|---|---|---|
| Additive (applied amount: wt.% relative to AI) | sodium silicate (5) | sodium silicate (2) sodium tripoly-phosphate (3) | — | sodium silicate (5) | sodium tripoly-phosphate (5) |
| Applied amount of $H_2O_2$ (wt.% relative to AI) | 5 | 5 | 1 | 1 | 1 |
| pH value of bleaching liquid | 10 | 10 | 8 | 10 | 8 |
| Temperature for bleaching treatment (°C.) | 80 | 80 | 80 | 80 | 80 |
| Time of bleaching (hr) | 2 | 2 | 2 | 2 | 2 |
| Color tone before bleaching (5% aqueous solution of AI) | 600 | 600 | 600 | 600 | 600 |
| Color tone after bleaching (5% aqueous solution of AI) | 70 | 50 | 380 | 150 | 200 |

|  | Example 16 | Example 17 |
|---|---|---|
| Additive (applied amount: wt.% relative to AI) | sodium tripoly-phosphate (3) sodium silicate (2) | sodium tripoly-phosphate (5) |
| Applied amount of $H_2O_2$ (wt.% relative to AI) | 1 | 0.5 |
| pH value of bleaching |  |  |

| | | |
|---|---|---|
| liquid | 10 | 8 |
| Temperature for bleaching treatment (°C.) | 80 | 80 |
| Time of bleaching (hr) | 2 | 3 |
| Color tone before bleaching (5% aqueous solution of AI) | 600 | 600 |
| Color tone after bleaching (5% aqueous solution of AI) | 140 | 290 |

(Remark)
Conditions for measurement of color tone:
  Sample: 5% aqueous solution of Sulfonate
  Method for measurement: absorptiometric method (using SPECTROPHOTOMETER MODEL-139, the manufacture of HITACHI Co., Ltd.)
  Wave-length: 420 mm
  Width of slit: 0.05 mm
  Indication of numerical value: actually measured absorbance $(-\log T) \times 10^3$

What is claimed is:

1. A process of bleaching water-soluble olefin sulfonates obtained by sulfonating olefins having from 12 to 22 carbon atoms, then neutralizing the sulfonation reaction product with caustic alkali and hydrolyzing, which consists essentially of: (1) adding to and dissolving thoroughly by mixing in an aqueous solution of said water-soluble olefin sulfonate, from 2 to 7 percent by weight, based on the weight of said olefin sulfonate, of a substance selected from the group consisting of sodium tripolyphosphate, potassium tripolyphosphate, sodium pyrophosphate, potassium pyrophosphate, sodium phosphate, potassium phosphate and mixtures thereof, the aqueous solution of said water-soluble olefin sulfonate and said substance having a pH of from 7 to 12 and being at a temperature in the range of from 30° to 130° C., (2) then adding to said aqueous solution of said water-soluble olefin sulfonate and said substance obtained in step (1), from more than 0.1 up to 10 percent by weight of hydrogen peroxide, based on the weight of said olefin sulfonate, and (3) maintaining the mixture obtained in step (2) at a temperature in said range for a period of time effective to bleach said olefin sulfonate.

2. A process according to claim 1, wherein the amount of said hydrogen peroxide is from 0.5% to 5 weight percent, based on the weight of said olefin sulfonate.

3. A process according to claim 1, wherein said olefin sulfonate is a sodium salt of α-olefin sulfonate having 16 to 18 carbon atoms.

4. A process according to claim 1, wherein the aqueous solution of said water-soluble olefin sulfonate and said substance is maintained at a temperature in the range of from 50° to 100° C. during steps (2) and (3).

5. A process according to claim 4 in which said substance is sodium tripolyphosphate.

* * * * *